United States Patent
Seok et al.

(10) Patent No.: US 10,243,141 B2
(45) Date of Patent: Mar. 26, 2019

(54) PRECURSOR OF INORGANIC/ORGANIC HYBRID PEROVSKITE COMPOUND

(71) Applicant: KOREA RESEARCH INSTITUTE OF CHEMICAL TECHNOLOGY, Daejeon (KR)

(72) Inventors: Sang Il Seok, Daejeon (KR); Jun Hong Noh, Daejeon (KR); Nam Joong Jeon, Gwangju (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 0 days.

(21) Appl. No.: 15/102,403

(22) PCT Filed: Dec. 23, 2014

(86) PCT No.: PCT/KR2014/012727
§ 371 (c)(1),
(2) Date: Jun. 7, 2016

(87) PCT Pub. No.: WO2015/099412
PCT Pub. Date: Jul. 2, 2015

(65) Prior Publication Data
US 2016/0322591 A1 Nov. 3, 2016

(30) Foreign Application Priority Data

Dec. 23, 2013 (KR) .................. 10-2013-0161888
Dec. 23, 2013 (KR) .................. 10-2013-0161911
Dec. 23, 2013 (KR) .................. 10-2013-0161916
May 9, 2014 (KR) .................. 10-2014-0055845

(51) Int. Cl.
| | | |
|---|---|---|
| H01L 51/42 | (2006.01) | |
| H01L 51/00 | (2006.01) | |
| C07F 7/24 | (2006.01) | |

(52) U.S. Cl.
CPC ........... *H01L 51/0007* (2013.01); *C07F 7/24* (2013.01); *H01L 51/0003* (2013.01); *H01L 51/0032* (2013.01); *H01L 51/4226* (2013.01); *H01L 2251/306* (2013.01); *Y02E 10/549* (2013.01)

(58) Field of Classification Search
CPC combination set(s) only.
See application file for complete search history.

(56) References Cited

U.S. PATENT DOCUMENTS

| | | | |
|---|---|---|---|
| 5,871,579 A | 2/1999 | Liang et al. | |
| 6,429,318 B1 | 8/2002 | Mitzi | |
| 2009/0095341 A1 | 4/2009 | Pfenninger et al. | |
| 2013/0139872 A1 | 6/2013 | Shum et al. | |
| 2013/0320836 A1* | 12/2013 | Kanatzidis | H01L 31/032 313/483 |
| 2015/0340632 A1* | 11/2015 | Etgar | H01L 51/4226 136/255 |

FOREIGN PATENT DOCUMENTS

| | | |
|---|---|---|
| CN | 103346018 A | 10/2013 |
| KR | 1020130110020 A | 9/2013 |
| KR | 1020130110025 A | 9/2013 |
| WO | 2013/171517 A1 | 11/2013 |
| WO | 2013/171520 A1 | 11/2013 |

OTHER PUBLICATIONS

Kojima et al. "Organometal Halide Perovskites as Visible-Light Sensitizers for Photovoltaic Cells," Apr. 2009.*
International Search Report dated Mar. 30, 2015; PCT/KR2014/012727.
Chinese Office Action dated Oct. 27, 2016; Appln. No. 201480070171.X.

* cited by examiner

Primary Examiner — Austin Murata
(74) Attorney, Agent, or Firm — Ladas & Parry LLP

(57) ABSTRACT

Provided is a precursor of an inorganic/organic hybrid perovskite compound, and the precursor of the precursor of the inorganic/organic hybrid perovskite compound according to an exemplary embodiment of the present invention includes an organic positive ion, a metal positive ion, a halogen negative ion, and a guest molecule (GM).

11 Claims, 3 Drawing Sheets

[FIG. 1]
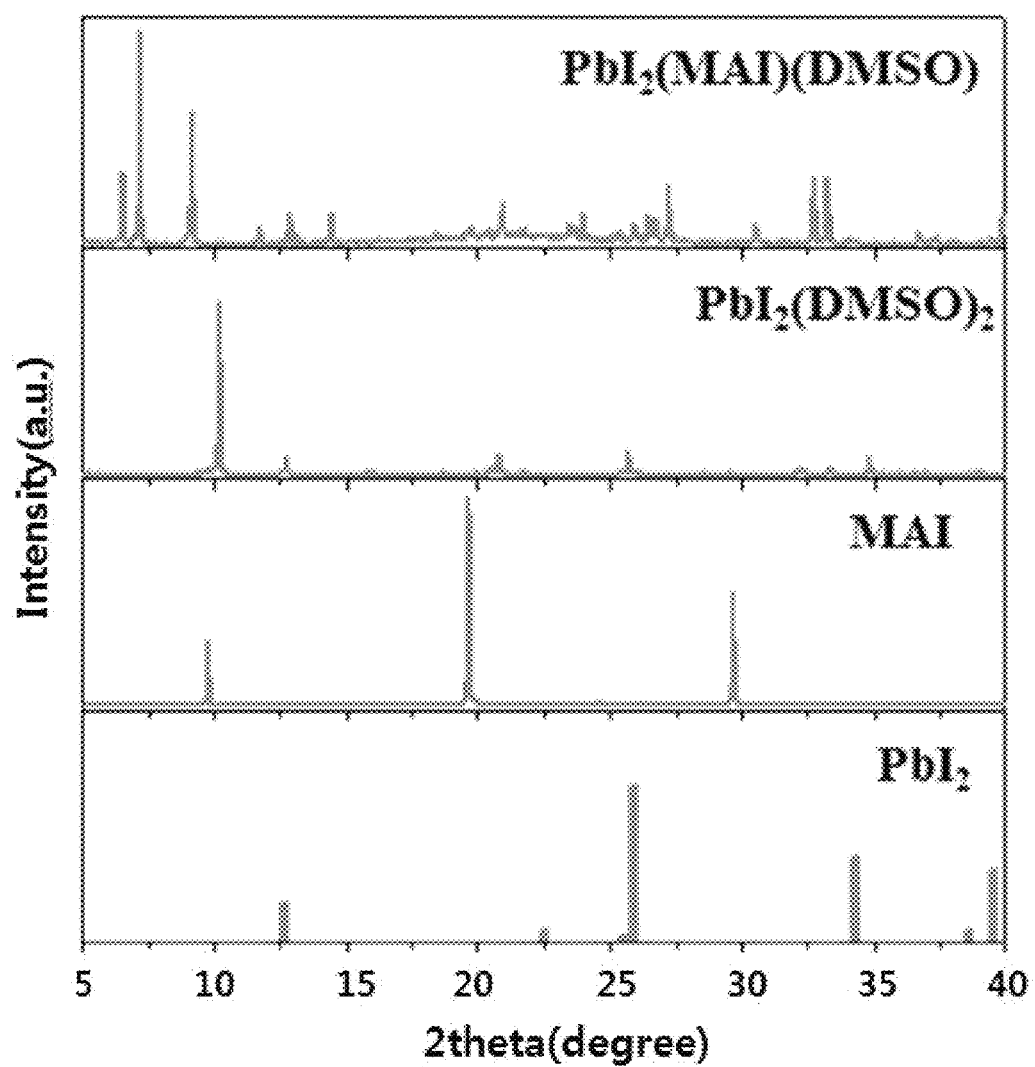

[FIG. 2]
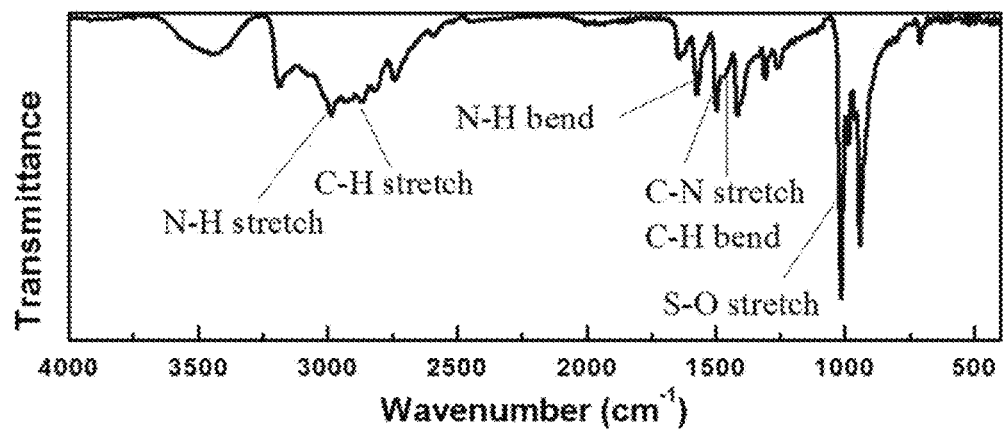
[FIG. 3]
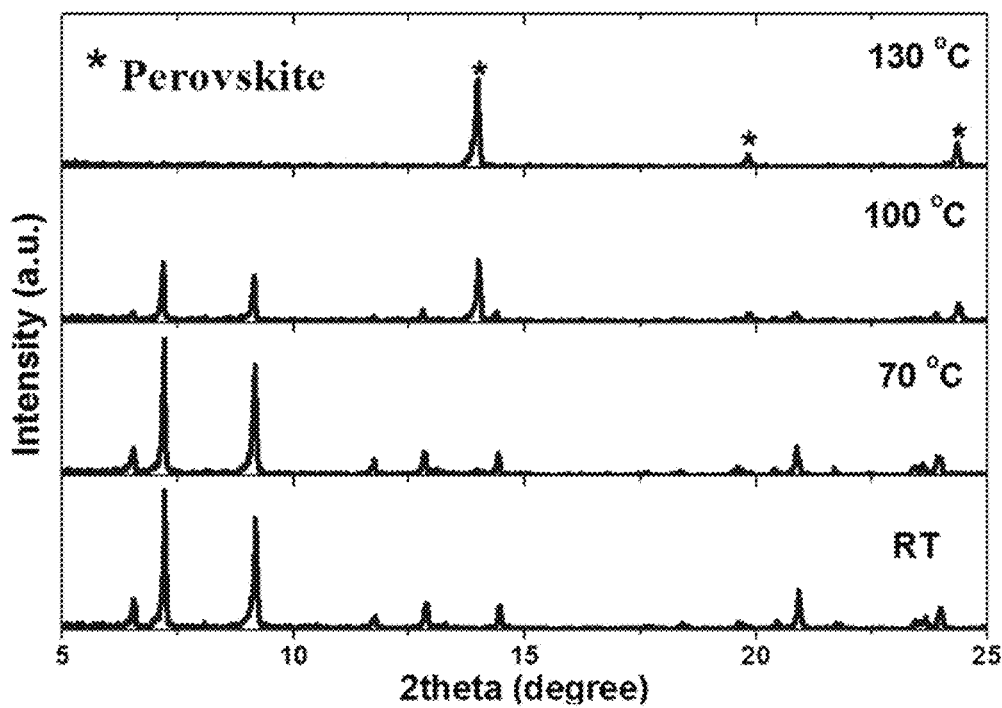

[FIG. 4]
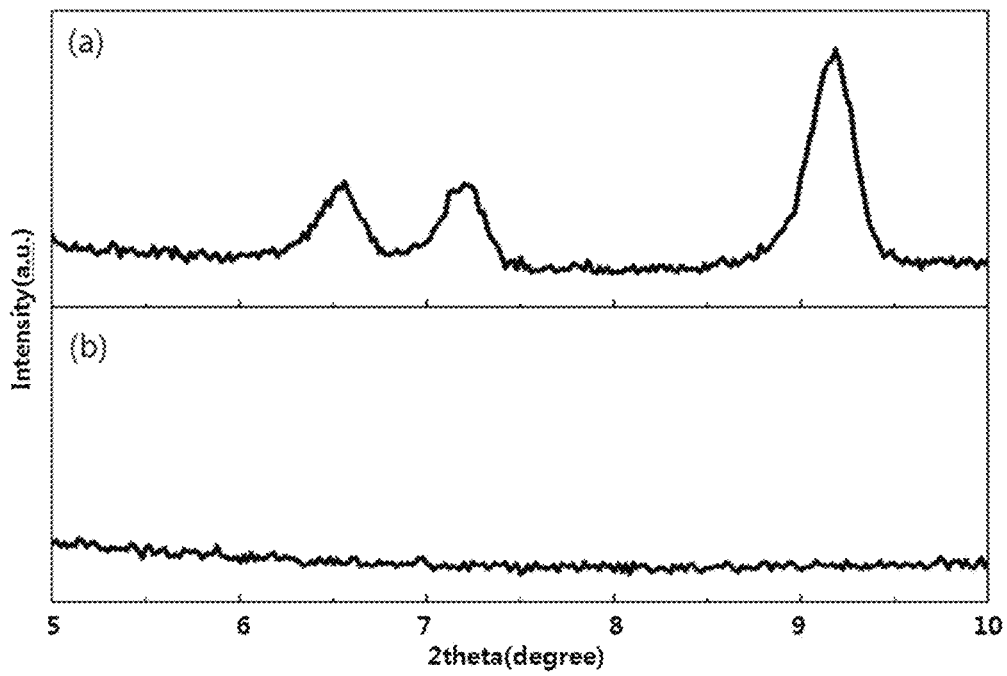
[FIG. 5]
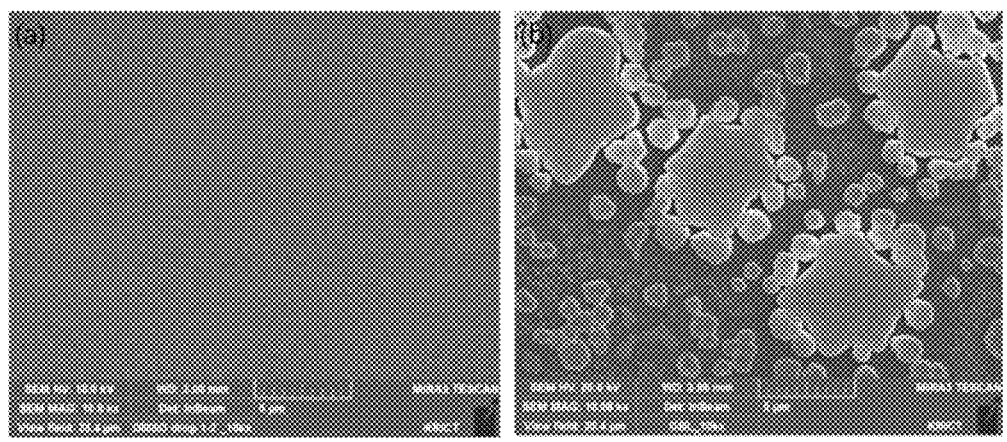

PRECURSOR OF INORGANIC/ORGANIC HYBRID PEROVSKITE COMPOUND

TECHNICAL FIELD

The present invention relates to a precursor of an inorganic/organic hybrid perovskite compound, and more particularly, to a precursor for a light absorber of a solar cell provided with an inorganic/organic hybrid perovskite compound as a light absorber.

BACKGROUND ART

An inorganic/organic hybrid perovskite compound, also referred to as an organometal halide perovskite compound, is represented by a chemical formula of $AMX_3$, consisting of an organic cation (A), a metal cation (M), and a halogen anion (X), and having a perovskite structure. Specifically, the inorganic/organic hybrid perovskite compound represented by a chemical formula of $AMX_3$ is in the form of a three-dimensional network in which an $MX_6$ octahedron is corner-shared, and A, an organic cation is positioned at the center. The inorganic/organic hybrid perovskite compound has a characteristic of self-assembling crystallization, and thus, is advantageous in that a low-temperature solution process is possible. However, the compound has a problem in that a crystallization rate is very high, and it is difficult to control the self-assembling characteristic, so that it is difficult to manufacture a dense thin film having a flat surface in practice.

In order to solve the problem, a sequential deposition method wherein a solution of metal halide ($MX_2$) is coated to form a metal halide film, an organic halide (AX) solution is coated on the metal halide film to form a laminate of $MX_2$ and AX films, and then the two films are reacted to form an inorganic/organic hybrid perovskite compound film, has been suggested (Chem. Mater. 13, 3283 (2001)). However, this sequential deposition method has problems in that firstly, the solubility of $MX_2$, represented by $PbI_2$ is not sufficiently high so that the manufacture of a thick metal halide film problematic; secondly, even in the case of maintaining a $MX_2$ solution at high temperature and coat it to obtain a thick film of 200 nm or more, $MX_2$ is not sufficiently reacted with AX in a reaction step due to its thickness; and thirdly, in the case of a film manufactured by a conventional sequential deposition method, large volume change is caused when two films are reacted, so that the surface of a finally obtained inorganic/organic hybrid perovskite compound film has very high roughness. Particularly, the roughness of a film surface may be a critical factor to lower a performance index of a cell, in a solar cell provided with an inorganic/organic hybrid perovskite compound film as a light absorbing layer.

DISCLOSURE

Technical Problem

An object of the present invention is to provide an inorganic/organic hybrid perovskite compound precursor capable of manufacturing an inorganic/organic hybrid perovskite compound film by a reaction, and a film thereof.

Specifically, an object of the present invention is to provide an inorganic/organic hybrid perovskite compound precursor capable of manufacturing a thick inorganic/organic hybrid perovskite compound film, a film of coarse crystal grains, and a film having a dense and smooth surface.

Another object of the present invention is to provide a method of manufacturing an inorganic/organic hybrid perovskite compound film using an inorganic/organic hybrid perovskite compound precursor.

Another object of the present invention is to provide a solar cell including an inorganic/organic hybrid perovskite compound film manufactured using an inorganic/organic hybrid perovskite compound precursor as a light absorbing layer, and a method of manufacturing the same.

Technical Solution

In one general aspect, a precursor of an inorganic/organic hybrid perovskite compound includes an organic cation, a metal cation, a halogen anion, and a guest molecule (GM).

In X-ray diffraction measurement of the precursor according to an exemplary embodiment of the present invention using a Cu-Kα ray, diffraction peaks at diffraction angles (2θ) of 6.2 to 6.8°, 7 to 7.5°, and 8.9 to 9.5° may be detected.

In the precursor according to an exemplary embodiment of the present invention, the guest molecule may be a solvent dissolving the inorganic/organic hybrid perovskite compound.

The precursor according to an exemplary embodiment of the present invention may be a solvate of the inorganic/organic hybrid perovskite compound and the solvent.

In the precursor according to an exemplary embodiment of the present invention, the guest molecule may be a solvent containing one or more elements selected from the group consisting of oxygen, nitrogen, fluorine, chlorine, bromine and iodine.

In the precursor according to an exemplary embodiment of the present invention, the guest molecule may be one or two or more selected from the group consisting of N,N-dimethylacetamid, 1,4-dioxane, diethylamine, ethylacetate, tetrahydrofuran, pyridine, methanol, ethanol, dichlorobenzene, glycerin, dimethyl sulfoxide (DMSO) and N,N-dimethylformamide (DMF).

The precursor according to an exemplary embodiment of the present invention may satisfy the following Chemical Formula 2:

$$AM(GM)_n X_3 \qquad \text{[Chemical Formula 2]}$$

wherein A is an organic ammonium ion, an amidinium group ion, or an organic ammonium ion and an amidinium group ion; M is a divalent metal ion; X is a halogen ion; and n is a real number of 0<n<3.

In the precursor according to an exemplary embodiment of the present invention, in Chemical Formula 1, X may be $X^a_{(1-y)} X^b_y$, wherein $X^a$ and $X^b$ are different halogen ions from each other, selected from the group consisting of an iodide ion (I⁻), a chloride ion (Cl⁻) and a bromide ion (Br⁻), and y is a real number of 0<y<1.

The precursor according to an exemplary embodiment of the present invention may be a precursor for a light absorber of a solar cell.

In another general aspect, a dispersion or an ink includes the above-described precursor.

In another general aspect, a method of manufacturing a light absorber of a solar cell uses the above-described precursor.

The method of manufacturing a light absorber according to an exemplary embodiment of the present invention may include: coating or vapor depositing the precursor on a base material to form a precursor layer; and applying energy on the precursor layer to volatilize and remove guest molecules.

Advantageous Effects

The precursor according to the present invention is a single precursor capable of preparing an inorganic/organic hybrid perovskite compound, and being converted into an inorganic/organic hybrid perovskite compound by removing guest molecules, and thus, has an advantage in that it is possible to manufacture an inorganic/organic hybrid perovskite compound film which is dense and has excellent crystallinity.

Further, it is also advantageous in that as a dense film of an inorganic/organic hybrid perovskite compound may be manufactured by an extremely simple process to remove guest molecules, a dense film of an inorganic/organic hybrid perovskite compound having high quality may be manufactured by a low-cost process, and as film quality is not sensitively changed depending on the change of process variables, it is very easy to maintain the quality, and it is possible to manufacture a dense film of an inorganic/organic hybrid perovskite compound having a large area.

Further, in the case of using the precursor according to the present invention, as a perfect film of a light absorber which is an inorganic/organic hybrid perovskite compound may be formed, the thin film formation of an inorganic/organic hybrid perovskite compound may be easily controlled, and thus, the precursor may be utilized in a variety of applications such as a thin film transistor, a light emitting diode, a sensor, a solar cell, and the like.

DESCRIPTION OF DRAWINGS

The above and other objects, features and advantages of the present invention will become apparent from the following description of preferred embodiments given in conjunction with the accompanying drawings, in which:

FIG. 1 is a drawing illustrating an X-ray diffraction result of precursor powder prepared according to an exemplary embodiment of the present invention.

FIG. 2 is a FTIR transmission spectrum of precursor powder prepared according to an exemplary embodiment of the present invention.

FIG. 3 is a drawing illustrating an X-ray diffraction result by temperature of precursor powder prepared according to an exemplary embodiment of the present invention.

FIG. 4 is a drawing illustrating an X-ray diffraction result of a precursor thin film manufactured according to an exemplary embodiment of the present invention.

FIG. 5 is a scanning electron micrograph observing a perovskite compound thin film manufactured from a precursor thin film manufactured according to an exemplary embodiment of the present invention.

BEST MODE

Hereinafter, the embodiments of the present invention will be described in detail with reference to accompanying drawings. The drawings to be provided below are provided by way of example so that the idea of the present invention may be sufficiently transferred to those skilled in the art to which the present invention pertains. Therefore, the present invention is not limited to the drawings provided below but may be modified in many different forms. In addition, the drawings suggested below will be exaggerated in order to clear the spirit and scope of the present invention. Technical terms and scientific terms used herein have the general meaning understood by those skilled in the art to which the present invention pertains unless otherwise defined, and a description for the known function and configuration unnecessarily obscuring the gist of the present invention will be omitted in the following description and the accompanying drawings.

The present invention includes the entire disclosures of Korean Patent Application Nos. 2013-0110020 and 2013-0110025.

The applicant of the present invention performed a lot of studies in order to improve efficiency of perovskite-based solar cell including an inorganic/organic hybrid perovskite compound as a light absorber, and as a result, has found out that photoelectric transformation efficiency of a solar cell is extremely significantly improved, when an inorganic/organic hybrid perovskite compound is in the form of a dense film having a smooth surface covering the porous electron carrier, while filling pores of a porous electron carrier.

One of the main advantages of the inorganic/organic hybrid perovskite compound is that a solution coating method may be used. However, in the case of using the solution coating method, a crystallization rate into the inorganic/organic hybrid perovskite compound is very high, and it is difficult to control a self-assembling characteristic, and thus, in reality, it is very difficult to manufacture a dense film having a smooth surface.

Based on the above discovery, as a result of putting in a great deal of effort to overcome the limitation of improving the film quality of the inorganic/organic hybrid perovskite compound film using the solution coating method, a precursor which allows the manufacture of the inorganic/organic hybrid perovskite compound film in the form of a dense film having high quality, while having the conventional advantages in the process of the inorganic/organic hybrid perovskite compound as they are, has been found out, thereby filing the present invention.

In the description of the present invention, the inorganic/organic hybrid perovskite compound may refer to a compound including a monovalent organic cation (A), a divalent metal cation (M), and a halogen anion (X), and having a perovskite structure.

Specifically, the inorganic/organic hybrid perovskite compound has a perovskite structure in which M is positioned at a center of a unit cell, X is positioned at a center of each face of a unit cell and forms an octahedron structure having M in the center, and A is positioned at each corner of a unit cell. More specifically, the structure is in the form of a three-dimensional network in which a $MX_6$ octahedron is corner-shared, and A, an organic cation is positioned at the center.

Hereinafter, the inorganic/organic hybrid perovskite compound is referred to as a perovskite compound. In addition, the precursor of the inorganic/organic hybrid perovskite compound is referred to as a precursor.

The perovskite compound may satisfy the following Chemical Formula 1:

$$AMX_3 \qquad \text{[Chemical Formula 1]}$$

wherein A is monovalent cation, which is an organic ammonium ion, an amidinium group ion, or an organic ammonium ion and an amidinium group ion; M is a divalent metal ion; and X is a halogen ion. Herein, the halogen ion may be one or two or more selected from the group consisting of $I^-$, $Br^-$, $F^-$ and $Cl^-$.

In Chemical Formula 1, the organic ammonium ion may satisfy the following Chemical Formulae 1-1 and 1-2:

$$R_1\text{—}NH_3^+ \qquad \text{[Chemical Formula 1-1]}$$

wherein $R_1$ is C1-C24 alkyl, C3-C20 cycloalkyl, or C6-C20 aryl.

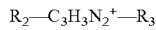  [Chemical Formula 1-2]

wherein $R_2$ is C1-C24 alkyl, C3-C20 cycloalkyl, or C6-C20 aryl; and $R_3$ is hydrogen or C1-C24 alkyl.

In Chemical Formula 1, the amidinium group ion may satisfy the following Chemical Formula 1-3:

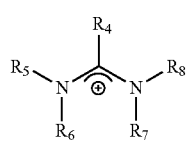  [Chemical Formula 1-3]

wherein $R_4$ to $R_8$ are independently of each other hydrogen, C1-C24 alkyl, C3-C20 cycloalkyl, or C6-C20 aryl.

In Chemical Formula 1, A may be an organic ammonium ion, an amidinium group ion, or an organic ammonium ion and an amidinium group ion. When A contains both the organic ammonium ion and the amidinium group ion, charge mobility of the perovskite compound may be significantly improved.

In the case that A contains both the organic ammonium ions and the amidinium group ion, 0.7 to 0.95 mol of the amidinium group ion and 0.3 to 0.05 mol of the organic ammonium ion may be contained, based on a total of 1 mol of the monovalent organic cation. That is, in Chemical Formula 1, A may be $A^a_{(1-x)}A^b_x$ in which $A^a$ is an amidinium group ion, $A^b$ is an organic ammonium ion, and x is a real number of 0.3 to 0.05. A mole ratio between the amidinium group ion and the organic ammonium ion, that is, a mole ratio of 0.7 to 0.95 mol of the amidinium group ion:0.3 to 0.05 mol of the organic ammonium ion is a range in which light of a very broad wavelength band may be absorbed, and more rapid movement and separation of excitons, and more rapid movement of photoelectrons and light holes may be made.

$R_1$ in Chemical Formula 1-1, $R_2$ and $R_3$ in Chemical Formula 1-2, and/or $R_4$-$R_8$ in Chemical Formula 1-3 may be properly selected depending on the use of the perovskite compound, that is, the use of the light absorbing layer of a solar cell, and the like.

Specifically, the perovskite compound has the size of the unit cell associated with a band gap, and may have band gap energy of 1.5-1.1 eV which is suitable for utilization as a solar cell in the small-sized unit cell. Accordingly, when band gap energy of 1.5-1.1 eV suitable for utilization as a solar cell is considered, in Chemical Formula 1-1, $R_1$ may be C1-C24 alkyl, specifically C1-C7 alkyl, more specifically, methyl. Further, in Chemical Formula 1-2, $R_2$ may be C1-C24 alkyl, $R_3$ may be hydrogen or C1-C24 alkyl, specifically $R_2$ may be C1-C27 alkyl, and $R_3$ may be hydrogen or C1-C7 alkyl, and more specifically $R_2$ may be methyl, and $R_3$ may be hydrogen. Further, in Chemical Formula 1-3, $R_4$ to $R_8$ may be independently of each other, hydrogen, amino, or C1-C24 alkyl, specifically hydrogen, amino, or C1-C7 alkyl, more specifically hydrogen, amino, or methyl, and still more specifically $R_4$ may be hydrogen, amino or methyl, and $R_5$ to $R_8$ may be hydrogen. As a specific and non-limiting example, the amidinium group ion may be a formamidinium ion ($NH_2CH=NH_2^+$), an acetamidinium ion ($NH_2C(CH_3)=NH_2^+$), guamidinium ion ($NH_2C(NH_2)=NH_2^+$), or the like.

As described above, specific examples of the organic cation (A) may be those considering the use of the perovskite compound film, that is, the use as the light absorbing layer of a solar cell, and $R_1$ in Chemical Formula 1-1, $R_2$ and $R_3$ in Chemical Formula 1-2, and/or $R_4$ to $R_8$ in Chemical Formula 1-3 may be appropriately selected, considering the design of a wavelength band of the light to be absorbed, the design of an emission wavelength band in the case of use as a light emitting layer of a light emitting element, an energy band gap and threshold voltage in the case of use as a semiconductor element of a transistor, and the like.

In Chemical Formula 1, M may be a divalent metal ion. As a specific example, M may be one or two or more metal ions selected from the group consisting of $Cu^{2+}$, $Ni^{2+}$, $Co^{2+}$, $Fe^{2+}$, $Mn^{2+}$, $Cr^{2+}$, $Pd^{2+}$, $Cd^{2+}$, $Ge^{2+}$, $Sn^{2+}$, $Pb^{2+}$ and $Yb^{2+}$.

In Chemical Formula 1, X may be a halogen anion. The halogen anion may be one or two or more selected from the group consisting of $I^-$, $Br^-$, $F^-$ and $Cl^-$. Specifically, the halogen anion may include one or two or more ions selected from the group consisting of an iodide ion ($I^-$), a chloride ion ($Cl^-$) and a bromide ion ($Br^-$). More specifically, the halogen anion may include an iodide ion and a bromide ion. When the halogen anion includes both an iodide ion and a bromide ion, the crystallinity and moisture resistance of the perovskite compound may be improved.

As a specific example, in Chemical Formula 1, X may be $X^a_{(1-y)}X^b_y$ in which $X^a$ and $X^b$ are different halogen ions from each other (different halogen ions from each other selected from the group consisting of iodide ion ($I^-$), chloride ion ($Cl^-$) and bromide ion ($Br^-$)), and y is a real number of $0<y<1$. More specifically, in Chemical Formula 1, X may be $X^a_{(1-y)}X^b_y$ in which $X^a$ is an iodide ion, $X^b$ is a bromide ion, and y is a real number of $0.05 \le y \le 0.3$, specifically, a real number of $0.1 \le x \le 0.15$. In this manner, deterioration by moisture may be significantly prevented, and the crystallinity of the perovskite compound may be improved.

Based on the above description, as an example of the specific and non-limiting perovskite compound in which M is $Pb^{2+}$, the perovskite compound may be $CH_3NH_3PbI_xCl_y$ (x is a real number of $0 \le x \le 3$, y is a real number of $0 \le y \le 3$, and x+y=3), $CH_3NH_3PbI_xBr_y$ (x is a real number of $0 \le x \le 3$, y is a real number of $0 \le y \le 3$, and x+y=3), $CH_3NH_3PbCl_xBr_y$ (x is a real number of $0 \le x \le 3$, y is a real number of $0 \le y \le 3$, and x+y=3), $CH_3NH_3PbI_xF_y$ (x is a real number of $0 \le x \le 3$, y is a real number of $0 \le y \le 3$, and x+y=3), $NH_2CH=NH_2PbI_xCl_y$ (x is a real number of $0 \le x \le 3$, y is a real number of $0 \le y \le 3$, and x+y=3), $NH_2CH=NH_2PbI_xBr_y$ (x is a real number of $0 \le x \le 3$, y is a real number of and $0 \le y \le 3$, x+y=3, $NH_2CH=NH_2PbCl_xBr_y$ (x is a real number of $0 \le x \le 3$, y is a real number of $0 \le y \le 3$, and x+y=3), $NH_2CH=NH_2PbI_xF_y$ (x is a real number of $0 \le x \le 3$, y is a real number of $0 \le y \le 3$, and x+y=3), $NH_2CH=NH_{2(1-x)}CH_3NH_{3x}Pb(I_{(1-y)}Br_y)_3$ (x is a real number of $0<x<1$, and y is a real number of $0<y<1$), $NH_2CH=NH_{2(1-x)}CH_3NH_{3x}Pb(I_{(1-y)}Br_y)_3$ (x is a real number of $0.05 \le x \le 0.3$, and y is a real number of $0.05 \le y \le 0.3$), $NH_2CH=CH_{2(1-x)}CH_3NH_{3x}Pb(I_{(1-x)}Br_x)_3$ (x is a real number of $0.05 \le x \le 0.3$), $NH_2C(CH_3)=NH_2PbI_xCl_y$ (x is a real number of $0 \le x \le 3$, y is a real number of $0 \le y \le 3$, and x+y=3), $NH_2C(CH_3)=NH_2PbI_xBr_y$ (x is a real number of $0 \le x \le 3$, y is a real number of $0 \le y \le 3$, and x+y=3), $NH_2C(CH_3)=NH_2PbCl_xBr_y$ (x is a real number of $0 \le x \le 3$, y is a real number of $0 \le y \le 3$, and x+y=3), $NH_2C(CH_3)=NH_2PbI_xF_y$ (x is a real number of $0 \le x \le 3$, y is a real number of $0 \le y \le 3$, and x+y=3), $NH_2C(CH_3)=NH_{2(1-x)}CH_3NH_{3x}Pb(I_{(1-y)}Br_y)_3$ (x is a real number of $0<x<3$, and y is a real number of $0<y<1$), $NH_2C(CH_3)=NH_{2(1-x)}CH_3NH_{3x}Pb(I_{(1-y)}Br_y)_3$ (x is a real number of $0.05 \le x \le 0.3$, y is a real number of $0.05 \leq y \leq 0.3$), $NH_2C(CH_3)=CH_{2(1-x)}$ $CH_3NH_{3x}Pb(I_{(1-x)}Br_x)_3$ (x is a real number of $0.05 \leq x \leq 0.3$), $NH_2C(NH_2)=NH_2PbI_xCl_y$ (x is a real number of $0 \leq x \leq 3$, y is a real number of $0 \leq y \leq 3$, and x+y=3), $NH_2C(NH_2)=NH_2PbI_xBr_y$ (x is a real number of $0 \leq x \leq 3$, y is a real number of $0 \leq y \leq 3$, and x+y=3), $NH_2C(NH_2)=NH_2PbCl_xBr_y$ (x is a real number of $0 \leq x \leq 3$, y is a real number of $0 \leq y \leq 3$, and x+y=3), $NH_2C(NH_2)=NH_2PbI_xF_y$ (x is a real number of $0 \leq x \leq 3$, y is a real number of $0 \leq y \leq 3$, and x+y=3), $NH_2C(NH_2)=NH_{2(1-x)}CH_3NH_{3x}Pb(I_{(1-y)}Br_y)_3$ (x is a real number of $0<x<1$, y is a real number of $0<y<1$), $NH_2C(NH_2)=NH_{2(1-x)}CH_3NH_{3x}Pb(I_{(1-y)}Br_y)_3$ (x is a real number of $0.05 \leq x \leq 0.3$, and y is a real number of $0.05 \leq y \leq 0.3$), or $NH_2C(NH_2)=CH_{2(1-x)}CH_3NH_{3x}Pb(I_{(1-x)}Br_x)_3$ (x is a real number of $0.05 \leq x \leq 0.3$).

The precursor according to an exemplary embodiment of the present invention is the precursor of the above-described perovskite compound, and contains an organic cation, a metal cation, a halogen anion (X), and a guest molecule (hereinafter, referred to as GM). In the precursor according to an exemplary embodiment of the present invention, the organic cation, metal ion and halogen anion contained in the precursor may be the same as the monovalent organic cation (A), divalent metal ion (M) and halogen anion (X) above described regarding the perovskite compound, and thus, detailed description therefor will be omitted.

In the crystal structure, the precursor may be an amorphous material, crystalline material, or a mixture of amorphous and crystalline materials. Specifically, the precursor may be crystalline.

Specifically, in X-ray diffraction measurement of the precursor according to an exemplary embodiment of the present invention using a Cu-Kα ray, diffraction peaks at diffraction angles (2θ) of 6.2 to 6.8°, 7 to 7.5°, and 8.9 to 9.5° may be detected. Herein, among the peaks at diffraction angles in a range of $5° \leq 2\theta \leq 40°$, the peaks at 8.9 to 9.5°, or 7 to 7.5° may have highest intensity.

The precursor according to an exemplary embodiment of the present invention may be in the form of a complex formed by GM coexisting with A (organic cation), M (metal cation) and X (halogen anion), which may prevent rapid conversion into a perovskite phase. That is, the precursor may be in the form of a complex formed by GM bonded to the perovskite compound ($AMX_3$) containing A (organic cation), M (metal cation) and X (halogen anion).

Specifically, the bond between the perovskite compound and GM may be a noncovalent bond, and GM may be in the state of being noncovalent-bonded to one or two or more cations selected from the group consisting of a monovalent organic cation (A) and a divalent metal cation (M).

In the precursor according to an exemplary embodiment of the present invention, the guest molecule may be a solvent dissolving the perovskite compound. Accordingly, the precursor may be a solvate of the perovskite compound and the solvent dissolving the compound. The solvate may refer to a compound of high order formed between the molecule or ion of a solute (perovskite compound) and the molecule or ion of the solvent.

Herein, the solvent dissolving the perovskite compound may refer to a polar organic solvent, and also refer to an organic solvent in which the solubility of the perovskite compound is 0.5 M or more, specifically 0.8 M or more at 20° C. and 1 atm.

When the precursor is a solvate of the perovskite compound and the solvent dissolving the compound, GM may be homogeneously and rapidly removed therefrom at a low temperature, so that the precursor is converted into the perovskite compound. Specifically, the precursor may be a solvate of the perovskite compound noncovalent-bonded to GM, the solvent, and GM may be a solvent containing one or more elements having an unshared electron pair selected from the group consisting of oxygen, nitrogen, fluorine, chlorine, bromine and iodine.

As an example of the solvent containing one or more elements selected from the group consisting of oxygen, nitrogen, fluorine, chlorine, bromine and iodine, and dissolving the perovskite compound, N,N-dimethylacetamide, 1,4-dioxane, diethylamine, ethylacetate, tetrahydrofuran, pyridine, methanol, ethanol, dichlorobenzene, glycerin, dimethyl sulfoxide (DMSO) and N,N-dimethylformamide (DMF), and a mixture thereof may be mentioned. That is, the guest molecule may be one or two or more selected from the group consisting of N,N-dimethylacetamide, 1,4-dioxane, diethylamine, ethylacetate, tetrahydrofuran, pyridine, methanol, ethanol, dichlorobenzene, glycerin, dimethyl sulfoxide (DMSO) and N,N-dimethylformamide (DMF). Herein, when the precursor is converted into the perovskite compound by removing GM, it is preferred that the guest molecule is dimethyl sulfoxide (DMSO), for preventing film quality from being damaged by volume change.

The precursor according to an exemplary embodiment of the present invention may satisfy the following Chemical Formula 2:

$$AM(GM)_nX_3 \qquad \text{[Chemical Formula 2]}$$

wherein A is an organic ammonium ion, an amidinium group ion, or an organic ammonium ion and an amidinium group ion; M is a divalent metal ion; X is a halogen ion; and n is a real number of $0<n<3$. Herein, in Chemical Formula 2, A, M and X are identical to A, M and X as described above regarding Chemical Formula 1.

That is, from the precursor according to Chemical Formula 2, GM is removed by external energy, and the precursor may be converted into the perovskite compound according to Chemical Formula 1.

Herein, as described above regarding the perovskite compound, in Chemical Formula 2, A may be $A^a_{(1-x)}A^b_x$ in which $A^a$ is amidinium group ion, $A^b$ is an organic ammonium ion, and x is a real number of $0<x<1$, specifically, a real number of $0.05 \leq x \leq 0.3$.

Independently of this, in Chemical Formula 2, X may be $X^a_{(1-y)}X^b_y$, wherein $X^a$ and $X^b$ are different halogen ions from each other, selected from the group consisting of an iodide ion ($I^-$), a chloride ion ($Cl^-$) and a bromide ion ($Br^-$), and y is a real number of $0<y<1$. Preferably, in Chemical Formula 2, X may be $X^a_{(1-y)}X^b_y$ in which $X^a$ is an iodide ion, $X^b$ is a bromide ion, and y is a real number of $0<y<1$, specifically, a real number of $0.05 \leq y \leq 0.3$, more specifically, a real number of $0.1 \leq x \leq 0.15$.

From the perovskite compound precursor according to an exemplary embodiment of the present invention, a guest molecule is removed by energy applied to the perovskite compound precursor, and the precursor may be changed to the crystalline perovskite compound.

That is, as the precursor is a complex compound of the perovskite compound and GM, the precursor may be converted into a pure perovskite compound by removing GM by applied energy.

The precursor according to an exemplary embodiment of the present invention may be a precursor for a light absorber of a solar cell.

The present invention provides a dispersion or an ink including the above-described precursor. Of course, the dispersion or ink may further include known additives together with the above-described precursor and dispersion medium, so as to have properties suitable for a coating or printing method.

The precursor may be prepared by the steps of adding dropwise a first solution containing an organic cation, a metal cation, a halogen ion and a guest molecule, according to the stoichiometric ratio of the perovskite compound into a non-solvent; and collecting and drying a solid phase obtained by the dropwise addition. As the precursor is a complex of the perovskite compound and GM, it may have similar or identical properties (such as solubility) to the perovskite compound, toward an organic solvent. Accordingly, a solvent dissolving a common perovskite compound may be used as a solvent of the first solution. The solvent dissolving the precursor may be any solvent as long as it dissolves the perovskite compound and is easily volatilized and removed. As a specific example, γ-butyrolactone (GBL), 1-methyl-2-pyrolidinone and the like may be mentioned, but the present invention is not limited thereto.

In the case that the precursor is a solvate, the solvent of the first solution may be the guest molecule. That is, the first solution may be prepared by dissolving an organic cation, a metal cation, and a halogen ion in a solvent which is the guest molecule.

Herein, as the precursor may have similar or identical properties (such as solubility) to the perovskite compound, toward the organic solvent, the non-solvent may refer to an organic solvent not dissolving the perovskite compound. Herein, an organic solvent "not dissolving the perovskite compound" means an organic solvent in which the perovskite compound has solubility less than 0.1 M, specifically less than 0.01 M, more specifically less than 0.001 M at 20° C. and 1 atm.

As an example of the non-solvent into which the first solution is added dropwise, a non-polar organic solvent may be mentioned, and the non-polar organic solvent may be one or two or more organic solvents selected from the group consisting of pentyne, hexane, cyclohexene, 1,4-dioxene, benzene, toluene, triethylamine, chlorobenzene, ethylamine, ethylether, chloroform, ethylacetate, acetic acid, 1,2-dichlorobenzene, tert-butylalcohol, 2-butanol, isopropanol and methylethylketone, but the present invention is not limited thereto. Herein, the concentration of solutes in the first solution may be increased to improve productivity, but the first solution may have any concentration, if the concentration satisfies the stoichiometric ratio within the range of the solubility of each solute.

The solid phase may be collected only using a general method used in a solid-liquid separation. As an example, filtering, centrifugation and the like may be mentioned, but not limited thereto. Drying may be carried out at any temperature, if the temperature is within the range not thermally damaging the precursor safely. As an example, the drying may be carried out at a room temperature to 50° C.

The present invention provides a method of manufacturing a light absorber of a solar cell using the above-described precursor.

The method of manufacturing a light absorber according to an exemplary embodiment of the present invention may include: coating or vapor depositing the precursor on a base material (substrate) to form a precursor layer; and applying energy on the precursor layer to volatilize and remove guest molecules.

As an example, after coating a solution in which the precursor is dissolved, or a dispersion or ink in which the perovskite compound precursor is dispersed on a base material (substrate), and then drying the coat to form a precursor layer, removing GM from the precursor layer, thereby converting the precursor layer into a perovskite compound layer.

As another example, when the precursor is a solvate, the perovskite compound, or the organic cation, the metal cation and the halogen ion according to the stoichiometric ratio of the perovskite compound are dissolved in a solvent which is a guest molecule (GM) to prepare a solution, and thereafter, the prepared solution is coated on a base material, and the non-solvent is coated on the coat again, thereby preparing the precursor layer containing the precursor.

Herein, the coating of the solution, dispersion or ink may be carried out by one or more methods selected from the group consisting of screen printing, spin coating, bar coating, gravure coating, blade coating, and roll coating, however, considering excellent commerciality to treat large area within a short time, spin coating is preferred.

The energy applied to the precursor layer may be thermal energy, light energy, vibrational energy, or the like. Applied energy intensity may be only at a level of breaking the bond between the perovskite compound and GM, and removing and volatilizing GM. As an example, the precursor may be heated to 100° C. or more, thereby converting the perovskite compound precursor into the perovskite compound, and furthermore, when the precursor layer is heated to 130° C. or more, it may be converted into the perovskite compound within a very short time. Herein, the upper limit of the heat treatment temperature for converting the precursor into the perovskite compound is only within the range not thermally damaging the base material on which the perovskite compound is intended to be formed. As an example, the heat treatment may be carried out at 100 to 200° C. Heat treatment time is only the time for sufficiently converting the precursor into the perovskite compound, considering the heat treatment temperature. As a non-limiting example, the heat treatment time may be 1 to 30 minutes, however, of course, the present invention is not limited thereto.

This may be illustrated by a reaction relationship as follows:

Reaction relationship: $A+M+3X+n(GM) \rightarrow AM$
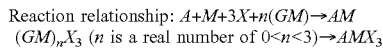$(GM)_n X_3$ ($n$ is a real number of $0<n<3$)$\rightarrow AMX_3$ When A, M and X in the solution is crystallized by volatilization and removal of the solvent so that $A+M+3X \rightarrow AMX_3$, it is difficult to control the kinetics of crystallization, and thus, it is difficult to form a dense perovskite compound film. In the reaction relationship of the precursor according to an exemplary embodiment of the present invention, the perovskite is not directly formed, and instead, the perovskite precursor ($AM(GM)_n X_3$) is firstly produced, and then the perovskite is formed by removing GM. Thus, since it is easy to control perovskite formation kinetics, the perovskite film which is dense and has a low surface roughness may be formed.

The base material on which the precursor layer is formed may be a base material on which other constitution (structure) is already formed in addition to the perovskite compound film, in a basic structure which an electronic device, an optical device, a solar cell, a sensor or the like essentially has for driving, depending on the use thereof.

Hereinafter, the detailed structure and method of manufacturing of a solar cell as an example will be described.

The base material may include a substrate being a supporter; a first electrode disposed on the substrate; and an electron carrier disposed on the first electrode.

That is, the base material on which the precursor layer is formed may include a laminate in which the substrate, the first electrode and the electron carrier are sequentially laminated.

The substrate may be a rigid or flexible substrate. As a specific example, the substrate may be a rigid substrate including a glass substrate, or a flexible substrate including polyethylene terephthalate (PET); polyethylene naphthalate (PEN); polyamide (PI); polycarbonate (PC); polypropylene (PP); triacetylcellulose (TAC); polyethersulfone (PES), and the like. However, the present invention is of course, not limited to those kinds of the substrates.

The first electrode may be any conductive electrode ohmic-contacted with the electron carrier, and any material commonly used as an electrode material of a front electrode or a back electrode in a solar cell may be used. As a non-limiting example, when the first electrode is the electrode material of a back electrode, it may be one or more materials selected from the group consisting of gold, silver, platinum, palladium, copper, aluminum, carbon, cobalt sulfide, copper sulfide, nickel oxide, and a composite thereof. As a non-limiting example, when the first electrode is a transparent electrode, it may be an inorganic-based conductive electrode such as a fluorine doped tin oxide (FTO), an indium doped tin oxide (ITO), ZnO, CNT (carbon nanotube) or graphene, or an organic-based conductive electrode such as PEDOT:PSS. In the case of providing a transparent solar cell, it is preferred that the first electrode is a transparent electrode, and in the case that the first electrode is the organic-based conductive electrode, it is more preferable for providing a flexible solar cell or a transparent solar cell.

The first electrode may be formed by vapor depositing or coating the electrode material on the substrate. Vapor deposition may be physical vapor deposition or chemical vapor deposition, and also carried out by thermal evaporation. Coating may be carried out by coating and then drying a solution of the electrode material or a dispersion of the electrode material on the substrate, or subjecting a dried film to heat treatment selectively. However, of course, the first electrode may be formed by a method used for formation of a front electrode or a back electrode in a general solar cell.

The electron carrier disposed on the first electrode may be an electron conductive organic layer, or an inorganic layer. The electron conductive organic material may be an organic material used as an n-type semiconductor, in a general organic solar cell. As a specific and non-limiting example, the electron conductive organic material may include fullerene (C60, C70, C74, C76, C78, C82, C95), fullerene-derivatives including PCBM ([6,6]-phenyl-$C_{61}$-butyric acid methyl ester), C71-PCBM, C84-PCBM, $PC_{70}BM$ ([6,6]-phenyl $C_{70}$-butyric acid methyl ester), PBI (polybenzimidazole), PTCBI (3,4,9,10-perylenetetracarboxylic bisbenzimidazole), F4-TCNQ (tetra uorotetracyanoquinodimethane), or a mixture thereof. The electron conductive inorganic material may be an electron conductive metal oxide used for electron transfer, in a general quantum dot based solar cell or dye-sensitized solar cell. As a specific example, the electron conductive metal oxide may be an n-type metal oxide semiconductor. As a non-limiting example of the n-type metal oxide semiconductor, one or two or more materials selected from the group consisting of Ti oxides, Zn oxides, In oxides, Sn oxides, W oxides, Nb oxides, Mo oxides, Mg oxides, Ba oxides, Zr oxides, Sr oxides, Yr oxides, La oxides, V oxides, Al oxides, Y oxides, Sc oxides, Sm oxides, Ga oxides, In oxides, and SrTi oxides may be mentioned, and also a mixture or a composite thereof may be mentioned.

In the structure, the electron carrier may be a porous layer or a dense layer. The dense electron carrier may be a film of the electron conductive organic material, or a dense film of the electron conductive inorganic material as described above. The porous electron carrier may be a porous film consisting of particles of the electron conductive inorganic material as described above. The electron carrier may be a thickness of 50 nm to 10 μm, specifically 50 nm to 1000 nm. If the electron carrier is porous, it has a specific surface area of 10 to 100 $m^2/g$, and the metal oxide particles forming the electron carrier may have an average diameter of 5 to 500 nm. The porous electron carrier may have porosity (apparent porosity) of 30% to 65%, specifically 40% to 60%.

In the case that the electron carrier has a porous structure, there may be further provided an electron carrying film between the first electrode and the electron carrier. The electron carrying film may serve to previously prevent the light absorber and the first electrode from being directly contacted to each other, and simultaneously to transport electrons. The electron carrying film may be any material as long as electrons are spontaneously movable from the porous metal oxide to the first electrode in the material, through the electron carrying film, in an energy band diagram. As a non-limiting and specific example, the electron carrying film may be the metal oxide thin film, and the metal oxide of the metal oxide thin film may be identical to or different from the metal oxide of the porous metal oxide. Specifically, the material of the metal oxide thin film may be one or more materials selected from the group consisting of Ti oxide, Zn oxides, In oxides, Sn oxides, W oxides, Nb oxides, Mo oxides, Mg oxides, Ba oxides, Zr oxides, Sr oxides, Yr oxides, La oxides, V oxides, Al oxides, Y oxides, Sc oxides, Sm oxides, Ga oxides, In oxides and SrTi oxides, and a mixture and a composite thereof. The electron carrying film may have a thickness of substantially 10 nm or more, more substantially 10 nm to 100 nm, still more substantially 50 nm to 100 nm.

The electron carrier may be formed by coating or vapor deposition. Specifically, the solution in which the electron carrier material is dissolved, or the dispersion (or slurry) in which the electron carrier material is dispersed is coated and dried, or a selectively dried product therefrom may be subjected to heat treatment, thereby preparing the electron carrier. The vapor deposition may be physical vapor deposition, or chemical vapor deposition.

As an example of the porous electron carrier, in more detail, the electron carrier may be prepared by coating, drying and heat-treating slurry containing metal oxide particles on the first electrode. The coating of the slurry may be carried out by one or more selected from the group consisting of screen printing, spin coating, bar coating, gravure coating, blade coating and roll coating.

However, of course, the electron carrier may be formed by a method of forming porous electron carrier of a metal oxide known in a general dye-sensitized solar cell or an organic solar cell.

Thereafter, a step to form the precursor layer on the porous electron carrier of the base material, as described above, and apply energy thereon to convert the precursor layer into the light absorbing layer of the perovskite compound, may be carried out.

The pores of the porous electron carrier may be filled, and the precursor layer may be formed in the form of a film covering the porous electron carrier, which is converted into the perovskite compound, thereby preparing the light absorbing layer having a structure of a dense film filling the pores of the porous electron carrier, and covering the entire surface of the porous electron carrier. Herein the dense film has a thickness of 1 nm to 10 μm.

Thereafter, on the dense film of the light absorbing layer, a step of sequentially forming a hole transporting layer and a second electrode may be carried out.

The hole transporting layer may include an organic hole transporting material, specifically a unimolecular to high molecular organic hole transporting material (hole conducting organic material). The organic hole transporting material may be any material as long as it is an organic hole transporting material used in a general inorganic semiconductor-based solar cell using an inorganic semiconductor quantum dot as dye. However, the high molecular organic hole transporting material is preferred in terms of energy matching with the light absorber which is the perovskite compound, and stability.

As a non-limiting example of the unimolecular to low molecular organic hole transporting material, one or two or more selected from the group consisting of pentacene, coumarin 6, 3-(2-benzothiazolyl)-7-(diethylamino)coumarin), ZnPC (zinc phthalocyanine), CuPC (copper phthalocyanine), TiOPC (titanium oxide phthalocyanine), Spiro-MeOTAD (2,2',7,7'-tetrakis(N,N-p-dimethoxyphenyl-amino)-9,9'-spirobifluorene), F16CuPC (copper(II) 1,2,3,4,8,9,10,11,15,16,17,18,22,23,24,25-hexadecafluoro-29H,31H-phthalocyanine), SubPc (boron subphthalocyanine chloride) and N3 (cis-di(thiocyanato)-bis(2,2'-bipyridyl-4,4'-dicarboxylic acid)-ruthenium(II)) may be mentioned, but not limited thereto.

The organic hole transporting material is preferably polymer (hole conducting polymer), which allows stable driving of the solar cell, and more improved generating efficiency by energy matching with the light absorber. Specifically, the hole conducting polymer may be one or two or more selected from the group consisting of thiophen-based, para-phenylenevinylene-based, carbazol-based, and triphenylamine-based polymers, and preferably, one or two or more selected from the group consisting of thiophene-based and triphenylamine-based polymers, and more preferably, a triphenylamine-based polymer. As a non-limiting example of the high molecular organic hole transporting material, one or two or more materials selected from the group consisting of P3HT (poly[3-hexylthiophene]), MDMO-PPV (poly[2-methoxy-5-(3',7'-dimethyloctyloxy)]-1,4-phenylene vinylene), MEH-PPV (poly[2-methoxy-5-(2'''-ethylhexyloxy)-p-phenylene vinylene]), P3OT (poly(3-octyl thiophene)), POT (poly(octyl thiophene)), P3DT (poly(3-decyl thiophene)), P3DDT (poly(3-dodecyl thiophene), PPV (poly(p-phenylene vinylene)), TFB (poly(9,9'-dioctylfluorene-co-N-(4-butylphenyl)diphenyl amine), Polyaniline, Spiro-MeOTAD ([2,22',7,77'-tetrkis (N,N-di-p-methoxyphenyl amine)-9,9,9'-spirobi fluorine]), PCPDTBT (Poly[2,1,3-benzothiadiazole-4,7-diyl[4,4-bis(2-ethylhexyl-4H-cyclopenta [2,1-b:3,4-b']dithiophene-2,6-diyl]], Si-PCPDTBT (poly[(4,4'-bis(2-ethylhexyl)dithieno[3,2-b:2',3'-d]silole)-2,6-diyl-alt-(2,1,3-benzothiadiazole)-4,7-diyl]), PBDTTPD (poly((4,8-diethylhexyloxyl) benzo([1,2-b:4,5-b']dithiophene)-2,6-diyl)-alt-((5-octylthieno[3,4-c]pyrrole-4,6-dione)-1,3-diyl)), PFDTBT (poly[2,7-(9-(2-ethylhexyl)-9-hexyl-fluorene)-alt-5,5-(4',7, -di-2-thienyl-2',1',3'-benzothiadiazole)]), PFO-DBT (poly[2,7-.9,9-(dioctyl-fluorene)-alt-5,5-(4',7'-di-2-thienyl-2',1',3'-benzothiadiazole)]), PSiFDTBT (poly[(2,7-dioctylsilafluorene)-2,7-diyl-alt-(4,7-bis(2-thienyl)-2,1,3-benzothiadiazole)-5,5'-diyl]), PSBTBT (poly[(4,4'-bis(2-ethylhexyl)dithieno[3,2-b:2',3'-d]silole)-2,6-diyl-alt-(2,1,3-benzothiadiazole)-4,7-diyl]), PCDTBT (Poly [[9-(1-octylnonyl)-9H-carbazole-2,7-diyl]-2,5-thiophenediyl-2,1, 3-benzothiadiazole-4,7-diyl-2,5-thiophenediyl]), PFB (poly (9,9'-dioctylfluorene-co-bis(N,N'-(4,butylphenyl))bis(N,N'-phenyl-1,4-phenylene)diamine), F8BT (poly(9,9'-dioctylfluorene-co-benzothiadiazole), PEDOT (poly(3,4-ethylenedioxythiophene)), PEDOT:PSS (poly(3,4-ethylenedioxythiophene) poly(styrenesulfonate)), PTAA (poly(triarylamine)), Poly(4-butylphenyl-diphenyl-amine), and a copolymer thereof, may be mentioned.

As a non-limiting and specific example, the hole transporting layer may have a thickness of 10 nm to 500 nm.

Of course, the hole transporting layer may further include an additive generally used for property improvement such as conductivity improvement of an organic-based hole conducting layer in an inorganic semiconductor-based solar cell using a general an inorganic semiconductor quantum dot as dye, or an organic solar cell. As a non-limiting example, the hole transporter may further include one or two or more additives selected from the group consisting of TBP (tertiary butyl pyridine), LiTFSI (Lithium Bis(Trifluoro methanesulfonyl)Imide) and Tris(2-(1H-pyrazol-1-yl)pyridine)cobalt (III), and may contain 0.05 mg to 100 mg of the additive per 1 g of the organic hole transporting material. However, of course, the present invention is not limited by the presence/absence of the additive, the kind of the additive, and the content of the additive in the hole transporting layer.

The second electrode may be any material as long as it is generally used as an electrode material of a front electrode or a back electrode in the solar cell. As a non-limiting example, when the second electrode is the electrode material of a back electrode, it may be one or more materials selected from the group consisting of gold, silver, platinum, palladium, copper, aluminum, carbon, cobalt sulfide, copper sulfide, nickel oxide, and a composite thereof. As a non-limiting example, when the second electrode is a transparent electrode, it may be an inorganic-based conductive electrode such as a fluorine doped tin oxide (FTP), an indium doped tin oxide (ITO), ZnO, CNT (carbon nanotube) or graphene, or an organic-based conductive electrode such as PEDOT:PSS. In the case of providing a transparent solar cell, it is preferred that the second electrode is a transparent electrode, and in the case that the second electrode is the organic-based conductive electrode, it is more preferable for providing a flexible solar cell or a transparent solar cell.

The second electrode may be formed by vapor deposition or coating. The vapor deposition may be physical vapor deposition or chemical vapor deposition, and also carried out by thermal evaporation. Coating may be carried out by coating and then drying a solution of the electrode material dissolved therein or a dispersion of the electrode material on the substrate, or subjecting a dried film to heat treatment selectively. However, of course, the second electrode may be formed by a method used for formation of a front electrode or a back electrode in a general solar cell.

The present invention provides a solar cell manufactured by the above manufacturing method.

The solar cell according to an exemplary embodiment of the present invention includes a substrate; a first electrode disposed on the substrate; a porous electron carrier disposed on the first electrode; a light absorbing layer including a perovskite compound in the form of a dense film filling the pores of the porous electron carrier and covering the porous electron carrier; a hole transporting layer disposed on the light absorbing layer; and a second electrode disposed on the hole transporting layer, wherein the perovskite compound may be produced by removing GM from a perovskite compound precursor.

The dense film of the perovskite compound in the light absorbing layer may have a thickness of 1 nm to 10 μm.

In description of the solar cell, the perovskite compound, the hole transporter, the electron carrier, the first electrode, the second electrode, the first substrate, and the second substrate are similar or identical to those described in the manufacturing method above, and thus, detailed description therefor will be omitted.

Comparative Example 1

$PbI_2$ powder was added to a dimethyl sulfoxide (DMSO) solvent, and stirred at 60° C. for 2 hours to prepare a 0.8 M $PbI_2$-DMSO solution. This solution was added dropwise to toluene, and then precipitated powder was separated and collected by filter paper, and dried at a room temperature for 1 hour.

Example 1

Preparation of Perovskite Precursor $CH_3NH_3I$ (hereinafter, referred to as MAI) and $PbI_2$ powders were added to a DMSO solvent in a stoichiometric ratio of 1:1, and stirred at 60° C. for 2 hours to prepare a 0.8 M $CH_2NH_3I$—$PbI_2$-DMSO solution. This solution was added dropwise to toluene, and then precipitated powder was separated and collected by filter paper, and dried at a room temperature for 1 hour.

The powder prepared in Comparative Example 1, MAI and $PbI_2$ which are precursors, and powder obtained in Example 1 were subjected to X-ray diffraction analysis using a Cu Kα ray, and the result is illustrated in FIG. 1.

As shown in FIG. 1, it is recognized that the powder prepared in Example 1 (indicated as $PbI_2$(MAI) (DMSO) in FIG. 1) does not contain the phases of MAI and $PbI_2$ materials which are precursors. Further, the powder prepared in Comparative Example 1 is reported by H. Miyamae as $PbI_2(DMSO)_2$ (Chemistry Lett., 9, 663, 1980). When comparing the result of XRD of this $PbI_2(DMSO)_2$ phase with that of the powder prepared in Example 1, and analyzing it, it is recognized that the powder obtained in Example 1 is not a $PbI_2(DMSO)_2$ phase. That is, it is recognized that the powder obtained in Example 1 has strong diffraction peaks at diffraction angle (2θ) of 6.2 to 6.8°, 7 to 7.5°, and 8.9 to 9.5°. Further, it is recognized that the powder obtained in Example 1 has a highest diffraction peak at 7 to 7.5°, in a range of 2θ of 5 to 40°. This XRD result shows that the powder prepared in Example 1 is a new compound completely different from the phases of MAI, $PbI_2$, $PbI_2(DMSO)_2$.

FIG. 2 represents the result of FTIR (Fourier transform infrared spectroscopy) of the powder prepared in Example 1. FIG. 2 indicates each absorption mode, and it is recognized that there is absorption of an S—O bond, a C—H bond, and a N—H bond, as shown in this IR transmission spectrum. This may be the evidence that the powder prepared in Example 1 includes both MAI and DMSO. In addition, it is recognized that the absorption by a C=C bond is not generated in FIG. 2, which shows that toluene is not contained in the powder. Through the results of XRD and FTIR, it is recognized that the powder obtained in Example 1 is a mixed crystal of MAI-$PbI_2$-DMSO.

For exact composition analysis, elemental analysis was carried out. As a result of the analysis, the weight ratio of each element was determined as being H=1.6%, C=4.6%, N=2.0%, O=2.2%, S=3.7%, based on which, the weight ratio of the residual elements was estimated to be 85.9%. Assuming that $CH_3NH_3I$, $PbI_2$ and $C_2H_6SO$(DMSO) in a mixed crystal are reacted with each other in a ratio of 1:1:1, the weight ratio will be H=1.7%, C=5.2%, N=2.0%, O=2.3%, S=4.6%, Pb=29.7%, I=54.5%, which is recognized to be similar to the measurement result of element analysis.

Thus, it is recognized therefrom that the powder prepared in Example 1 is a crystal formed by the reaction of 1:1:1 MAI-$PbI_2$-DMSO, which is MAPb$(C_2H_6SO)I_3$(=$C_3H_{12}$NSOPb$I_3$). This may be an example of AM(GM)nX$_3$ suggested in Chemical Formula 2 wherein A is MA, M is Pb, GM is DMSO, X is I, and n is 1.

In order to examine the transition of this MAPb(DMSO)$I_3$ perovskite precursor to a pure perovskite phase, XRD analysis according to heat treatment temperature was carried out, and the result is illustrated in FIG. 3. The XRD analysis was carried out in-situ, by maintaining for 1 minute for each temperature range as shown, and then performing the analysis. It is recognized from FIG. 3 that at a room temperature (RT), a pure MAPb(DMSO)$I_3$ perovskite precursor phase is maintained, as in the result in FIG. 1. However, as the heat treatment temperature increases, the precursor is converted into the perovskite phase. In the XRD spectrum at 100° C., it is shown that as the strength of the peaks below 10° which are the characteristic peaks of the precursor becomes weak, a peak near 14° which is the characteristic peak of perovskite simultaneously appears. This result shows that GM was removed by thermal energy up to 100° C., and the perovskite precursor was converted into pure perovskite. In addition, it is shown that at 130° C., only a pure perovskite diffraction peak is observed, which indicates that pure perovskite was formed from the precursor. That is, it is recognized that DMSO which had been present as GM was completely removed therefrom, thereby forming pure perovskite.

Example 2

Preparation of Precursor Thin Film

A MAI-$PbI_2$-DMSO solution was prepared by using the method presented in Example 1, except that γ-butyrolactone (GBL) was used as an additional mixed solvent. That is, the solution was prepared in a 0.8 M concentration based on MAPb$I_3$, with a volume ratio of GBL:DMSO of 7:3.

On a fused silica substrate, the prepared MAI-$PbI_2$-DMSO solution (total 1 ml) was coated (injected) batchwise on a rotation center, and started spin coating at 5000 rpm. At the point of 50 seconds after starting spin coating, 1 ml of a non-solvent, toluene was coated (injected) batchwise again on a rotation center of a porous electrode being rotated, and then spin coating proceeded for further seconds. After completing spin coating, drying was carried out at a room temperature for 1 hour. Thereafter, under the condition of a temperature of 100° C. and ambient pressure, heat treatment was carried out for 30 minutes to form a light absorber which is a perovskite compound thin film. During the manufacture of the light absorber thin film, the surrounding environment was maintained at a temperature of 25° C. and relative humidity at 25%.

Comparative Example 2

A thin film was manufactured in the same manner as Example 1, expect that only 100% γ-butyrolactone (hereinafter, referred to as GBL) was used, without DMSO (MAI-$PbI_2$-GBL solution) when preparing the solution.

FIG. 4 is an XRD spectrum of the thin film manufactured prior to heat treatment at 100° C. in Example 2 (FIG. 4(a)) and Comparative Example 2 (FIG. 4(b)). This result shows that in Example 2, a specific peak of the precursor was observed in the manufactured thin film, however, in the case of using pure GBL, this peak was not observed. That is, in Example 2, it is recognized that the film of MAPb(DMSO)I$_3$ perovskite precursor was formed.

FIG. 5 is a scanning electron micrograph of the perovskite film after heat treatment in Example 2 (FIG. 5(a)) and Comparative Example 2 (FIG. 5(b)). In Example 2, according to the above-described reaction relationship, the perovskite compound was formed via a precursor step, and in Comparative Example 2, the perovskite compound was directly formed in the solution. As shown in FIG. 5, when the precursor thin film is changed to the perovskite film, the perovskite compound is in the form of a dense and complete film.

Example 3

Manufacture of Porous TiO$_2$ Thin Film Substrate

A glass substrate on which a fluorine-containing tin oxide was coated (FTO; F-doped SnO$_2$, 8 ohms/cm$^2$, Pilkington, hereinafter, referred to as FTO substrate (first electrode)) was cut into a size of 25×25 mm, and then an end portion thereof was etched, thereby partially removing FTO.

On the cut and partially etched FTO substrate, a TiO$_2$ dense film having a thickness of 50 nm was manufactured by spray pyrolysis, as a metal oxide thin film. The spray pyrolysis was carried out using a TAA (Titanium acetylacetonate):EtOH (1:9 v/v %) solution, and the thickness was adjusted in a manner of repeating the process of spraying the solution for 3 seconds, and stopping for 10 seconds, on the FTO substrate placed on a hotplate maintained at 450° C.

An ethyl cellulose solution in which 10 wt % of ethyl cellulose was dissolved in ethyl alcohol was added to TiO$_2$ powder (prepared by hydrothermal treatment of an aqueous titanium peroxocomplex solution in which 1 wt % is dissolved based on TiO$_2$, at 250° C. for 12 hours) having an average particle size (diameter) of 50 nm, at 5 ml per 1 g of TiO$_2$ powder, terpinol was added thereto and mixed at 5 g per 1 g of TiO$_2$ powder, and ethyl alcohol was removed by distillation under reduced pressure, thereby preparing TiO$_2$ paste.

Ethanol was added to the prepared TiO$_2$ powder paste (weight ratio of 1 (TiO$_2$ powder paste):3 (ethanol)) to prepare TiO$_2$ slurry for spin coating. On the TiO$_2$ thin film on the FTO substrate, the TiO$_2$ slurry for spin coating was spin coated at 1000 rpm. Thereafter, heat treatment at 500° C. for 60 minutes was carried out, and then the heat-treated substrate was immersed in a 30 mM TiCl$_4$ aqueous solution at 60° C., stood for 30 minutes, washed with distilled water and ethanol, dried, and heat-treated again at 500° C. for 30 minutes, thereby manufacturing a porous TiO$_2$ thin film (porous electron carrier) having a thickness of 300 nm. The manufactured porous electron carrier had a specific surface area of 33 m$^2$/g, and a porosity (apparent porosity) of 50%.

The fused silica in Example 2 was replaced with the manufactured porous electron carrier, thereby manufacturing the light absorbing layer of the perovskite compound on the porous electron carrier, in the same manner as in Example 2. Thereafter, on the light absorbing layer, a toluene solution [15 mg (PTAA)/1 mL] in which PTAA poly(triarylamine), EM index, Mw=17,500 g/mol) is dissolved was spin-coated at 3000 rpm for 60 minutes, thereby forming a hole transporting layer. Herein, 2.31 mg of LiTFSI (Lithium Bis(Trifluoro methanesulfonyl)Imide) and 6.28 mg of TBP (tertiary butyl pyridine) were added to the PTAA solution. Thereafter, Au was vacuum vapor deposited on the hole transporting layer by a thermal evaporator of high vacuum (5×10$^{-6}$ torr or less) to form an Au electrode (second electrode) having a thickness of 70 nm, thereby manufacturing a solar cell.

Comparative Example 3

The solar cell was manufactured in the same manner as in Example 3, except that the fused silica in Example 2 was replaced with the manufactured porous electron carrier, thereby manufacturing the light absorbing layer of the perovskite compound on the porous electron carrier, in the same manner as in Comparative Example 2.

The photoelectric conversion properties of the solar cells manufactured in Example 3 and Comparative Example 3 were measured under the condition of AM 1.5 (100 mA/cm$^2$), and the result is shown in Table 1. The perovskite compound film manufactured in Example 3 was in the form of a dense thin film covering 100% of the upper surface of the electron carrier, however, the perovskite compound film in Comparative Example 3 was in the form of an incomplete film not covering 100% of the upper surface of the electron carrier. Accordingly, better Jsc, Voc, and FF values, and excellent photoelectric conversion efficiency were shown in Example 3.

TABLE 1

Performance index of solar cell manufactured in Example 3 and Comparative Example 3

|  | Jsc (mA/cm$^2$) | Voc (V) | FF | PCF (%) |
| --- | --- | --- | --- | --- |
| Example 3 | 19.8 | 1.10 | 0.75 | 16.3 |
| Comparative Example 3 | 18.7 | 0.96 | 0.70 | 12.6 |

Hereinabove, although the present invention has been described by specific matters, exemplary embodiments, and drawings, they have been provided only for assisting in the entire understanding of the present invention. Therefore, the present invention is not limited to the exemplary embodiments. Various modifications and changes may be made by those skilled in the art to which the present invention pertains from this description.

Therefore, the spirit of the present invention should not be limited to the above-described exemplary embodiments, and the following claims as well as all modified equally or equivalently to the claims are intended to fall within the scope and spirit of the invention.

The invention claimed is:

1. An inorganic/organic hybrid perovskite compound precursor comprising an organic cation (A), a metal cation (M), a halogen anion (X), and a guest molecule (GM), satisfying Chemical Formula 2:

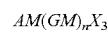

$AM(GM)_nX_3$ wherein n is a real number of 0<n<3, and being a solvate of the inorganic/organic hybrid perovskite compound and the guest molecule, and
being a solid phase material,
wherein the precursor is in powder form.

2. The precursor of claim 1, wherein in X-ray diffraction measurement of the precursor using a Cu-Kα ray, diffraction peaks at diffraction angles (2θ) of 6.2 to 6.8°, 7 to 7.5°, and 8.9 to 9.5° are detected.

3. The precursor of claim 1, wherein the guest molecule is a solvent dissolving the inorganic/organic hybrid perovskite compound.

4. The precursor of claim 3, wherein the guest molecule is a solvent containing one or more elements selected from the group consisting of oxygen, nitrogen, fluorine, chlorine, bromine and iodine.

5. The precursor of claim 3, wherein the guest molecule is one or two or more selected from the group consisting of N,N-dimethylacetamid, 1,4-dioxane, diethylamine, ethylacetate, tetrahydrofuran, pyridine, methanol, ethanol, dichlorobenzene, glycerin, dimethyl sulfoxide (DMSO) and N,N-dimethylformamide (DMF).

6. The precursor of claim 3, wherein A is an organic ammonium ion, an amidinium group ion, or an organic ammonium ion and an amidinium group ion; M is a divalent metal ion; and X is a halogen ion.

7. The precursor of claim 6, wherein in Chemical Formula 2, X is $X^a_{(1-y)}X^b_y$, in which $X^a$ and $X^b$ are different halogen ions from each other, selected from the group consisting of an iodide ion ($I^-$), a chloride ion ($Cl^-$) and a bromide ion ($Br^-$), and y is a real number of $0<y<1$.

8. The precursor of claim 3, wherein the guest molecule is one or two or more selected from the group consisting of N,N-dimethylacetamid, 1,4-dioxane, diethylamine, ethylacetate, tetrahydrofuran, pyridine, methanol, ethanol, dichlorobenzene, glycerin and dimethyl sulfoxide (DMSO).

9. The precursor of claim 1, wherein the precursor is for a light absorber of a solar cell.

10. A method of manufacturing a light absorber of a solar cell using the precursor of claim 1, comprising:
   coating or vapor depositing the precursor on a base material to form a precursor layer; and
   applying energy on the precursor layer to volatilize and remove guest molecules.

11. The precursor of claim 1, wherein the precursor is crystalline.

* * * * *